(12) United States Patent
Chen et al.

(10) Patent No.: US 9,076,237 B2
(45) Date of Patent: Jul. 7, 2015

(54) SYSTEM AND METHOD FOR ESTIMATING A STATISTICAL NOISE MAP IN X-RAY IMAGING APPLICATIONS

(71) Applicant: Wisconsin Alumni Research Foundation, Madison, WI (US)

(72) Inventors: Guang-Hong Chen, Madison, WI (US); Jie Tang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 310 days.

(21) Appl. No.: 13/796,783

(22) Filed: Mar. 12, 2013

(65) Prior Publication Data

US 2014/0270454 A1 Sep. 18, 2014

(51) Int. Cl.
- G06T 5/00 (2006.01)
- G06T 5/50 (2006.01)
- A61B 6/03 (2006.01)
- A61B 6/00 (2006.01)

(52) U.S. Cl.
CPC . *G06T 5/50* (2013.01); *G06T 5/002* (2013.01); *G06T 2207/10081* (2013.01); *G06T 2207/10112* (2013.01); *G06T 2207/10116* (2013.01); *G06T 2207/20216* (2013.01); *A61B 6/032* (2013.01); *A61B 6/508* (2013.01); *A61B 6/5205* (2013.01); *A61B 6/5258* (2013.01)

(58) Field of Classification Search
CPC .......... G06T 5/001; G06T 5/002; G06T 5/50; G06T 7/0012; G06T 2207/10116; G06T 2207/20216; G06T 2207/20224; G06K 9/40; G06K 2209/05; A61B 5/7203; A61B 6/5205; A61B 6/5211; A61B 6/5258; A61B 6/5282
See application file for complete search history.

(56) References Cited

U.S. PATENT DOCUMENTS

| | | | | |
|---|---|---|---|---|
| 6,314,160 B1 * | 11/2001 | Dhawale et al. | ............ | 378/98.2 |
| 6,493,416 B1 * | 12/2002 | Hsieh | ................ | 378/4 |
| 8,194,937 B2 | 6/2012 | Chen | ............... | 332/118 |
| 8,229,199 B2 | 7/2012 | Chen et al. | .................... | 382/130 |
| 8,374,413 B2 | 2/2013 | Chen | ............................ | 382/131 |
| 2009/0135998 A1 * | 5/2009 | Rossl et al. | ..................... | 378/98 |
| 2014/0005971 A1 * | 1/2014 | Roessl et al. | ........... | G01T 7/005 |

OTHER PUBLICATIONS

Yu, et al., Fast Model-Based X-Ray CT Reconstruction Using Spatially Nonhomogeneous ICD Optimization, IEEE Transactions on Image Processing, 2011, 20(1):161-175.

\* cited by examiner

*Primary Examiner* — Andrew W Johns

(74) *Attorney, Agent, or Firm* — Quarles & Brady, LLP

(57) ABSTRACT

Described here are a system and method for producing a statistical noise map that indicates the noise present in data acquired with an x-ray imaging system, such as an x-ray computed tomography system, an x-ray tomosynthesis system, a C-arm x-ray imaging system, and so on. In general, an image is reconstructed from the acquired data using, for example, any standard filtered back projection ("FBP") image reconstruction algorithm. This image is used as a base line to estimate a noise standard distribution map. The raw projection data represents a typical measurement among many repeated measurements under the same experimental conditions; therefore, the measured projection data can be used to numerically generate an ensemble of many (e.g., twenty or more) noisy projection data sets. These noisy projection data sets are then used to reconstruct noisy images and from these noisy images and the original image, the statistical noise map can be computed.

23 Claims, 3 Drawing Sheets

SYSTEM AND METHOD FOR ESTIMATING A STATISTICAL NOISE MAP IN X-RAY IMAGING APPLICATIONS

STATEMENT REGARDING FEDERALLY SPONSORED RESEARCH

This invention was made with government support under EB009699 awarded by the National Institutes of Health. The government has certain rights in the invention.

BACKGROUND OF THE INVENTION

The field of the invention is system and methods for x-ray imaging. More particularly, the invention relates to systems and methods for estimating a map of noise statistics in data acquired with an x-ray imaging system such that the noise map can be implemented to account for noise during an iterative image reconstruction.

Iterative image reconstructions, including both algebraic reconstruction and statistical image reconstruction frameworks, have been used for reconstructing high quality tomographic images from severely noise contaminated projection data. It has been known that a statistical weight is critical for great image quality; however, using existing methods for producing noise maps, the data acquisition process must be repeated many times to obtain a good estimate of the statistical noise. This has been a bottleneck for image quality improvement, especially when balanced against the desire to reduce x-ray radiation dose.

It would therefore be desirable to provide a system or method for estimating a statistical noise map that does not require multiple data acquisitions that result in a higher x-ray dose exposure to the imaged subject.

SUMMARY OF THE INVENTION

The present invention overcomes the aforementioned drawbacks by providing a system and method for estimating a statistical noise map from a single x-ray exposure.

It is an aspect of the invention to provide a method for producing a statistical noise map using an x-ray imaging system. Data that indicates a count of photons detected by the x-ray imaging system is acquired, and from this data an image is reconstructed. Noisy data is formed by adding statistical noise to the acquired data. From this noisy data, a noisy image is reconstructed. A statistical noise map is then produced by subtracting the reconstructed image and the noisy image.

It is another aspect of the invention to provide a method for iteratively reconstructing an image of a subject from data acquired with an x-ray imaging system. Data that indicates a count of photons detected by the x-ray imaging system is acquired from a subject, and from this data an image is reconstructed. Noisy data is formed by adding statistical noise to the acquired data. From this noisy data, a noisy image is reconstructed. A statistical noise map is then produced using the reconstructed image and the noisy image. An image of the subject is reconstructed from the acquired data using an iterative image reconstruction that accounts for a physical model of noise in the acquired data by using the produced statistical noise map.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are a system and method for producing a statistical noise map that indicates the noise present in data acquired with an x-ray imaging system, such as an x-ray computed tomography system, an x-ray tomosynthesis system, a C-arm x-ray imaging system, and an on-board imager, such as a cone-beam CT imaging system using in image guided radiation therapy. In general, the method includes reconstructing an image from acquired data using, for example, any standard filtered back projection ("FBP") image reconstruction algorithm. This image is used as a base line to estimate a noise standard distribution map. The raw projection data represents a typical measurement among many repeated measurements under the same experimental conditions; therefore, the measured projection data can be used to numerically generate an ensemble of many (e.g., twenty or more) noisy projection data sets. These noisy projection data sets are then used to reconstruct noisy images, using the same FBP image reconstruction algorithms.

Using these images with added noise, a standard deviation map of the original noise can be generated. This standard deviation map can be generated using a statistical process over the ensemble of noisy images, or can be performed using a statistical process over a spatial region-of-interest using only a single noisy image. After the noise standard deviation map is obtained, a forward projection operation is used to generate the corresponding uncertainty of the projection data.

The system and method of the present invention is capable of producing a statistical noise map from only a single acquisition, thereby reducing the x-ray dose imparted to the subject compared to other noise estimation methods. Using the system and method of the present invention, statistical image reconstruction can also be performed in a new rectified data acquisition geometry that significantly accelerates reconstruction speed.

Figure 1:
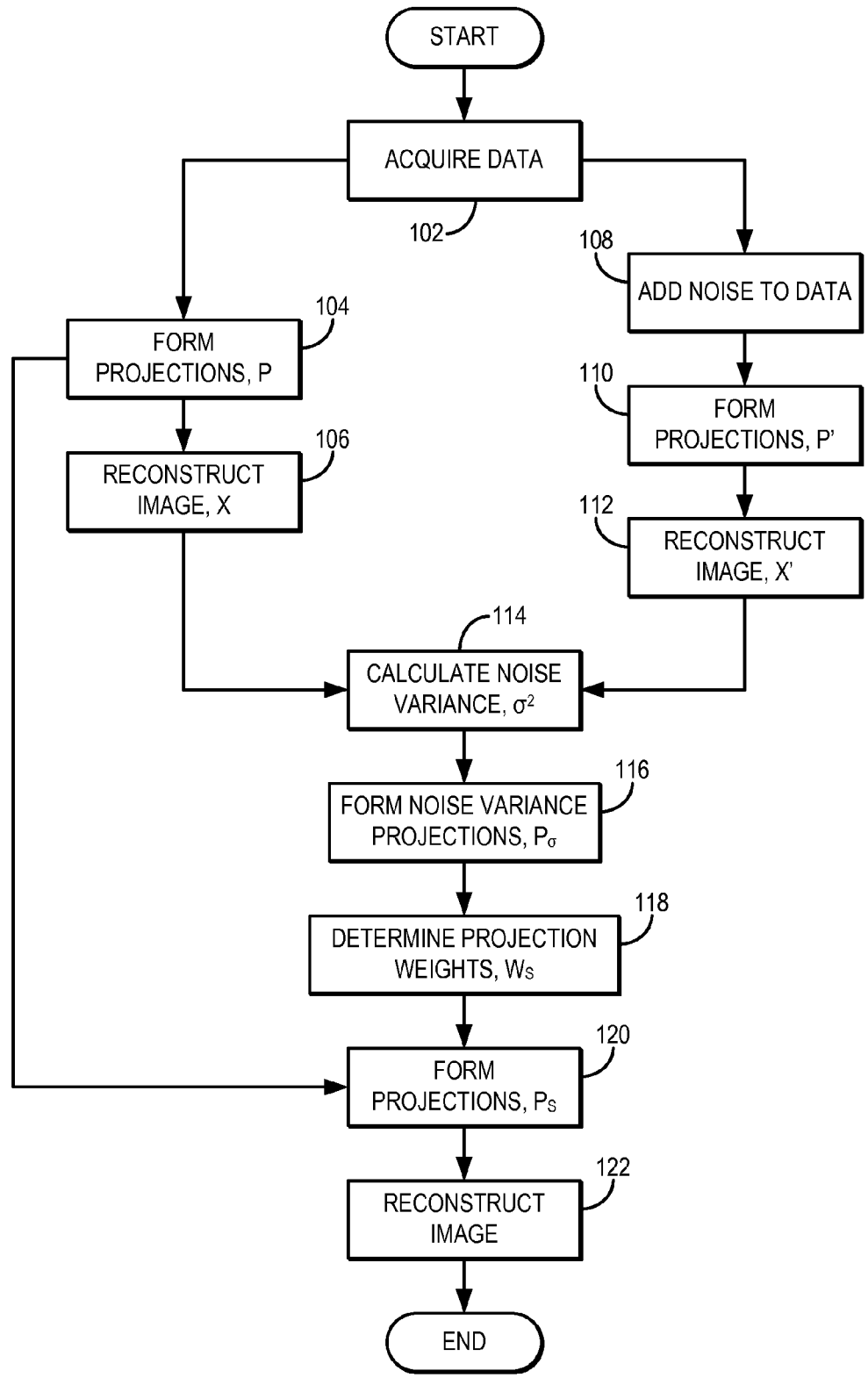
FIG. 1 is a flowchart setting forth the steps of an example of a method for producing a statistical noise map from a single data acquisition and for using that statistical noise map in an iterative image reconstruction.

Referring now to FIG. 1, a flowchart setting forth the steps of an example of a method for producing a statistical noise map from a limited amount of data is illustrated. One advantage of this method is that the subject does not need to be subjected to repeated measurements and thus x-ray exposures in order to obtain the statistical noise map. Rather, only one exposure is necessary. As also illustrated in FIG. 1, this statistical noise map can then advantageously be used in an iterative image reconstruction method.

The method begins with acquiring data with an x-ray system, as indicated at step 102. Preferably, this data is acquired with an x-ray computed tomography system, but may also be acquired using an x-ray tomosynthesis system, a C-arm x-ray imaging system, or an on-board imaging system in an image guided radiation therapy system. The acquired data is stored as counts of photons impinging on an x-ray detector. As indicated at step 104, the projections, P, are formed from the acquired data in the traditional sense. From this x-ray projection data, an image, X, is reconstructed, as indicated at step 106. The image reconstruction performed in step 106 can be performed using any suitable reconstruction technique, such as a simple filtered backprojection.

As indicated at step 108, the acquired data is also processed by adding noise to the detector counts. By way of example, Poisson noise is added to the acquired data. From the noise-added data, noise-added projections, P', are formed, as indicated at step 110. From these noise-added projections, a noise-added image, X', is reconstructed, as indicated at step 112. Like above, this noise-added image can be produced using any suitable image reconstruction method, such as filtered backprojection. Steps 108-112 can be repeated to using different Poisson noise statistics in each repetition of step 108 in order to produce a plurality of noise-added images, $X'_i$, with i=1, 2, ..., N. Alternatively, to reduce the computational burden associated with computing multiple different noise-added images, only one noise-added image, X', can be produced.

The image, X, and the one or more noise-added images, $X'_i$, are then used to estimate the noise variance, $\sigma^2$, in the acquired data, as indicated at step 114. By way of example, a noise distribution map, $\sigma^2(X, y)$, can be calculated according to the following equation:

$$\sigma^2(x, y) = \frac{1}{N-1} \sum_{i=1}^{N} (X'_i - X)^2. \quad (1)$$

As another example, the noise distribution map can also be produced by performing a statistical procedure over a spatial region of interest. The latter technique is less computationally burdensome than the averaging process in Eqn. (1), but is also less accurate due to the existence of spatial correlations in the reconstructed images. After the noise distribution map is produced, noise variance projections, $P_\sigma$, can be formed by forward projecting the noise distribution map, as indicated at step 116. These noise variance projections, $P_\sigma$, indicate the corresponding uncertainty (standard deviation) of the projection data, P, formed in step 104.

From the generated noise variance projections, $P_\sigma$, projection weights, $W_s$, can be determined, as indicated at step 118. These projections weights, $W_s$, are defined by a generally monotonically decreasing function that assigns a small weight to data with a high level of uncertainty and a large weight to data with a low level of uncertainty. It is noted that these statistical weights can be obtained for data from any data acquisition geometry, regardless of the specific scanner hardware configuration used to acquire the data in step 102. This rectification of the data acquisition geometry significantly broadens the applicability of these statistical weights to not only iterative image reconstruction algorithms based on raw projection data, but also to iterative image reconstruction algorithms that are based in the image domain, as will be described below.

One example form of the statistical projection weights is as follows:

$$W_s = W_{s,min} + \left(\frac{P_{\sigma,max} - P_\sigma}{P_{\sigma,max} - P_{\sigma,min}}\right)^2 \cdot (W_{s,max} - W_{s,min}); \quad (2)$$

where $W_{s,min}$ is the value of the weight that corresponds to the smallest uncertainty in the data; $W_{s,max}$ is the value of the weight that corresponds to the highest uncertainty in the data; $P_\sigma$ is a value of the noise variance projection; $P_{\sigma,min}$ is the minimum value of the noise variance projections; and $P_{\sigma,max}$ is the maximum value of the noise variance projections. Another example form of the statistical projection weights is as follows:

$$W_s = e^{-2\left(\frac{P_\sigma - P_{\sigma,min}}{P_{\sigma,max} - P_{\sigma,min}}\right)}. \quad (3)$$

The calculated projection weights, $W_s$, can then be used to form weighted projections by applying the weights to the projections formed in step 104, as indicated at step 120. These weighted projections can then be used in an iterative image reconstruction method to reconstruct an image of the subject, as indicated at step 122. By way of example, the image reconstruction performed in step 122 can be an iterative image reconstruction technique that operates in projection space using the true experimental data pertinent to a specific hardware data acquisition system, or an iterative reconstruction technique that operates in synthetic projection space that is generated from an initially reconstructed image via a forward projection step. The latter scheme does not depend on the original hardware data acquisition scheme. By way of example, the forward projection step can be used to rectify the original data acquisition method into the simplest parallel beam data acquisition geometry in order to simplify the image reconstruction. In those instances, the present invention enables an image denoising process to be incorporated into the image reconstruction process, thereby allowing the preservation of spatial resolution during the denoising process. By way of example, the spatial resolution of the original image can be encoded into the synthetics projection data. The iterative reconstruction can then be designed with an appropriate selection of regularization such that noise is lowered in the reconstructed images while iteratively restoring the spatial resolution of the target image from the high resolution synthetic projection data. An example of such an approach is a prior image constrained compressed sensing method, such as those described in U.S. Pat. Nos. 8,194,937; 8,229,199; and 8,374,413, which are each herein incorporated by reference in their entirety.

Figure 2A:
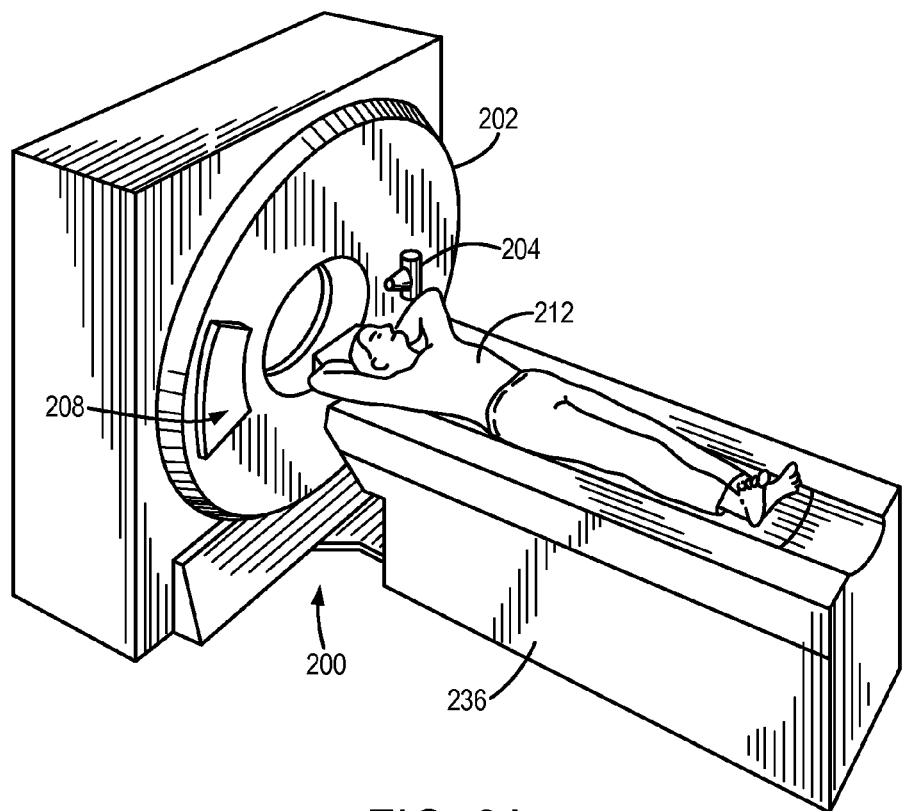
FIG. 2A is an illustration of an example of an x-ray computed tomography system.
Figure 2B:
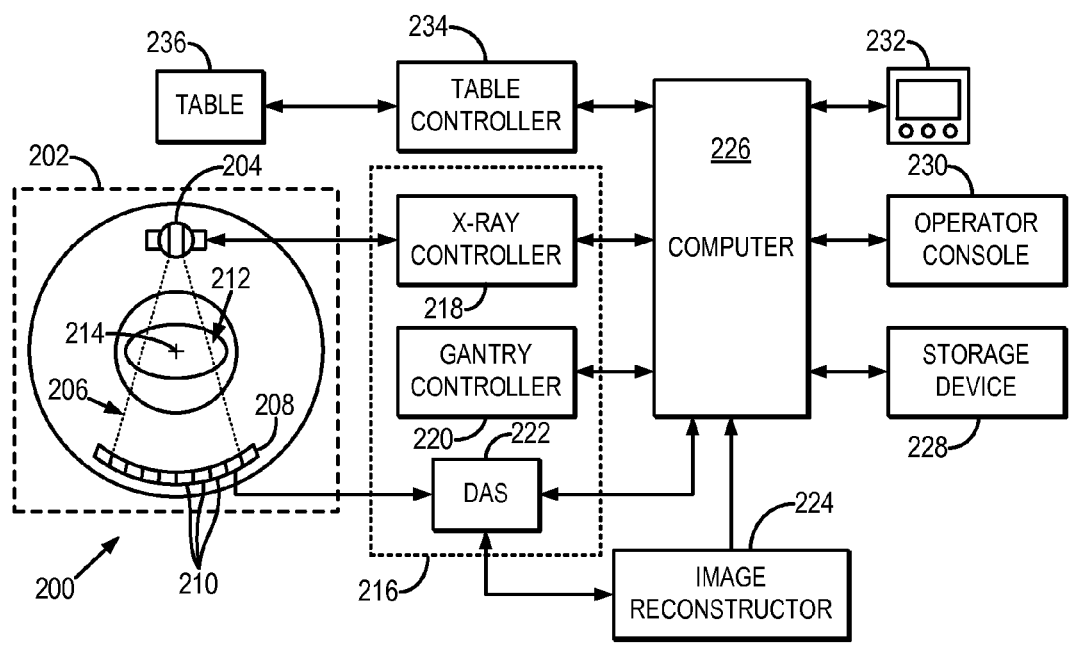
FIG. 2B is a block diagram of the x-ray CT system of FIG. 2A.

With initial reference to FIGS. 2A and 2B, an x-ray computed tomography ("CT") imaging system 200 that may be used when practicing the present invention includes a gantry 202. The gantry 202 has an x-ray source 204 that projects a fan-beam, or cone-beam, of x-rays 206 toward a detector array 208 on the opposite side of the gantry 202. The detector array 208 is formed by a number of detector elements 210, which together sense the projected x-rays 206 that pass through a subject 212, such as a medical patient or an object undergoing examination. Each detector element 210 produces an electrical signal that represents the intensity of an impinging x-ray beam and, hence, the attenuation of the beam as it passes through the subject 212. During a scan to acquire x-ray projection data, the gantry 202 and the components mounted thereon rotate about a center of rotation 214 located within the subject 212.

The rotation of the gantry 202 and the operation of the x-ray source 204 are governed by a control mechanism 216 of the CT system 200. The control mechanism 216 includes an x-ray controller 218 that provides power and timing signals to the x-ray source 204, and a gantry controller 220 that controls the rotational speed and position of the gantry 202. A data acquisition system ("DAS") 222 in the control mechanism 216 samples data from the detector elements 210 and converts the data to digital signals for subsequent processing. An image reconstructor 224, receives sampled and digitized x-ray data from the DAS 222 and performs image reconstruction thereon. The reconstructed image is applied as an input to a computer 226 which stores the image in a storage device 228, such as a mass storage device.

The computer 226 also receives commands and scanning parameters from an operator via a console 230 that has a keyboard. An associated display 232 allows the operator to observe the reconstructed image and other data from the computer 226. The operator supplied commands and parameters are used by the computer 226 to provide control signals and information to the DAS 222, the x-ray controller 218, and the gantry controller 220. In addition, computer 226 operates a table controller 234 that controls a table 236 to position the subject 212 in the gantry 202.

Figure 3A:
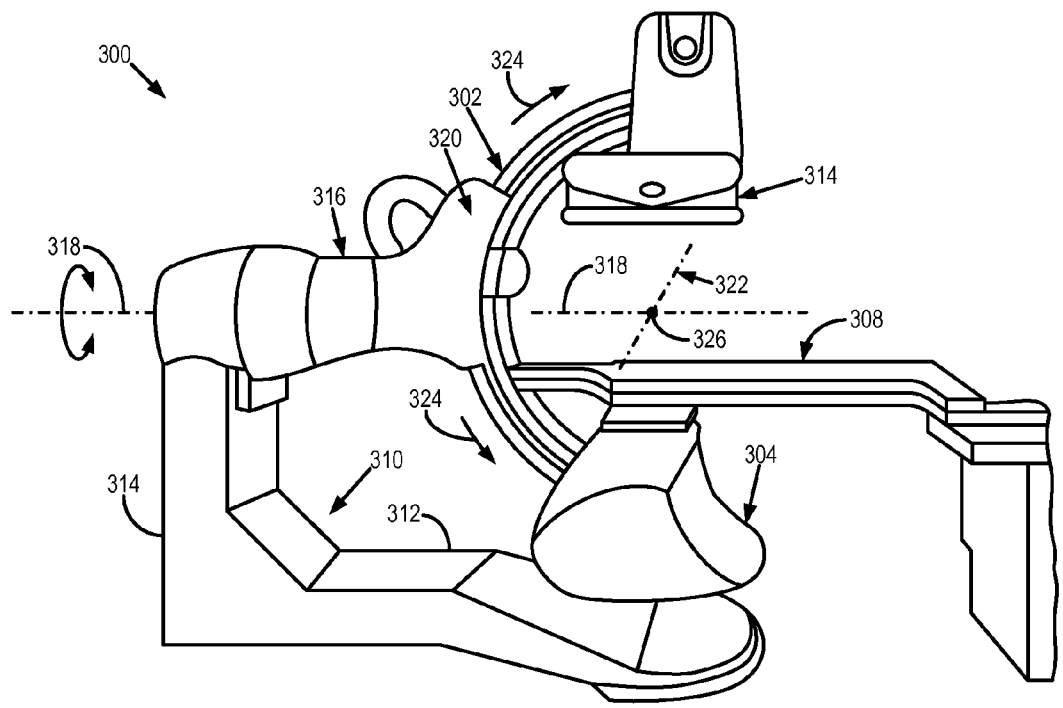
FIG. 3A is an illustration of an example of a C-arm x-ray imaging system.
Figure 3B:
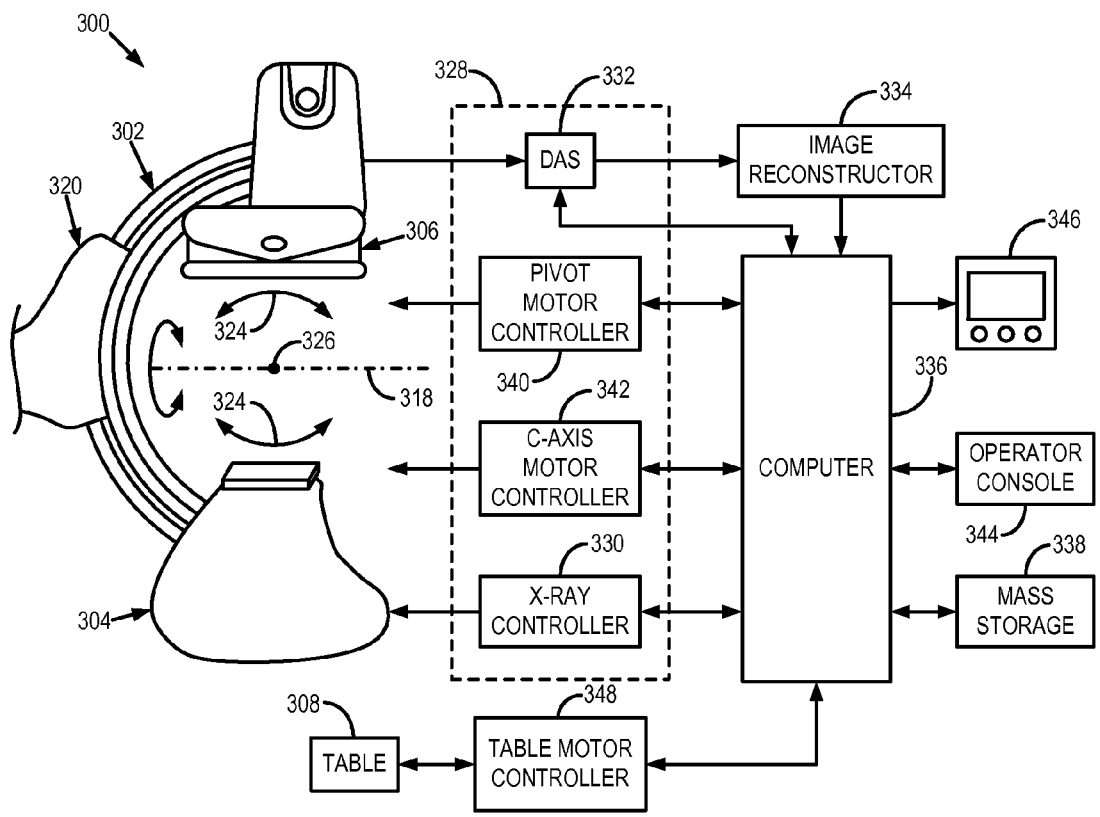
FIG. 3B is a block diagram of the C-arm x-ray imaging system of FIG. 3A.

Referring particularly to FIGS. 3A and 3B, an example of a so-called "C-arm" x-ray imaging system 300 is illustrated. Such an imaging system 300 is generally designed for use in connection with interventional procedures. The imaging system 300 is characterized by a gantry having a C-arm 302 that carries an x-ray source assembly 302 on one of its ends and an x-ray detector array assembly 306 at its other end. The gantry enables the x-ray source assembly 303 and detector array assembly 306 to be oriented in different positions and angles around a patient disposed on a table 308, while enabling a physician access to the patient.

The gantry includes a support base 310, which may include an L-shaped pedestal that has a horizontal leg 312 that extends beneath the table 308 and a vertical leg 314 that extends upward at the end of the horizontal leg 312 that is spaced from of the table 308. A support arm 316 is rotatably fastened to the upper end of vertical leg 314 for rotation about a horizontal pivot axis 318. The pivot axis 318 is aligned with the centerline of the table 308 and the support arm 316 extends radially outward from the pivot axis 318 to support a C-arm drive assembly 320 on its outer end. The C-arm 302 is slidably fastened to the drive assembly 320 and is coupled to a drive motor (not shown) that slides the C-arm 302 to revolve it about a C-axis 322, as indicated by arrows 324. The pivot axis 318 and C-axis 322 intersect each other at an isocenter 326 that is located above the table 308 and they are perpendicular to each other.

The x-ray source assembly 304 is mounted to one end of the C-arm 302 and the detector array assembly 306 is mounted to its other end. As will be discussed in more detail below, the x-ray source assembly 304 includes an x-ray source (not shown) that emits a cone beam of x-rays, which are directed at the detector array assembly 306. Both assemblies 304 and 306 extend radially inward to the pivot axis 318 such that the center ray of this cone beam passes through the system isocenter 326. The center ray of the cone beam can, thus, be rotated about the system isocenter 326 around either the pivot axis 318, the C-axis 322, or both during the acquisition of x-ray attenuation data from a subject placed on the table 308.

As mentioned above, the x-ray source assembly 304 contains an x-ray source that emits a cone beam of x-rays when energized. The center ray passes through the system isocenter 326 and impinges on a two-dimensional flat panel digital detector housed in the detector assembly 306. Examples of flat panel detectors include so-called "small flat panel" detectors, in which the detector array panel is around 20×20 centimeters in size. Such a detector panel allows the coverage of a field-of-view of around twelve centimeters. Each detector element produces an electrical signal that represents the intensity of an impinging x-ray and, hence, the attenuation of the x-ray as it passes through the patient. During a scan, the x-ray source and detector array are rotated about the system isocenter 326 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed.

Referring particularly to FIG. 3B, the rotation of the assemblies 304 and 306 and the operation of the x-ray source are governed by a control mechanism 328 of the imaging system 300. The control mechanism 328 includes an x-ray controller 330 that provides power and timing signals to the x-ray source. A data acquisition system ("DAS") 332 in the control mechanism 328 samples data from detector elements in the detector array and passes the data to an image reconstructor 334. The image reconstructor 334, receives digitized x-ray data from the DAS 332 and performs image reconstruction. The image reconstructed by the image reconstructor 334 is applied as an input to a computer 336, which stores the image in a mass storage device 338 or processes the image further.

The control mechanism 328 also includes pivot motor controller 340 and a C-axis motor controller 342. In response to motion commands from the computer 336, the motor controllers 340 and 342 provide power to motors in the imaging system 300 that produce the rotations about the pivot axis 318 and C-axis 322, respectively. A program executed by the computer 336 generates motion commands to the motor controllers 340 and 342 to move the assemblies 304 and 306 in a prescribed scan path.

The computer 336 also receives commands and scanning parameters from an operator via a console 344 that has a keyboard and other manually operable controls. An associated display 346 allows the operator to observe the reconstructed image and other data from the computer 336. The operator supplied commands are used by the computer 336 under the direction of stored programs to provide control signals and information to the DAS 332, the x-ray controller 330, and the motor controllers 340 and 342. In addition, the computer 336 operates a table motor controller 348, which controls the patient table 308 to position the patient with respect to the system isocenter 326.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a statistical noise map using an x-ray imaging system, the steps of the method comprising:
    a) acquiring data with the x-ray imaging system, the acquired data indicating a count of photons detected by the x-ray imaging system;
    b) reconstructing an image from the data acquired in step a);
    c) forming noisy data by adding statistical noise to the data acquired in step a);

d) reconstructing a noisy image from the noisy data formed in step c); and e) producing a statistical noise map by subtracting the image reconstructed in step b) and the noisy image reconstructed in step d).

2. The method as recited in claim 1 in which the noisy data formed in step c) comprises a plurality of noisy data sets, each noisy data set being formed by adding different statistical noise to the data acquired in step a).

3. The method as recited in claim 2 in which step d) includes reconstructing a plurality of noisy images from the noisy data, each noisy image being reconstructed from a corresponding noisy data set.

4. The method as recited in claim 3 in which step e) includes producing a plurality of statistical noise maps that each depict substantially only noise, each statistical noise map being produced by subtracting one of the plurality of noisy images reconstructed in step d) from the image reconstructed in step b).

5. The method as recited in claim 4 further comprising calculating a noise variance from the plurality of statistical noise maps produced in step e).

6. The method as recited in claim 5 in which the noise variance is calculated by calculating an average of a sum of squares calculated using the image reconstructed in step b) and each of the plurality of noisy images.

7. The method as recited in claim 6 in which the average of a sum of squares is calculated according to:

$$\frac{1}{N-1}\sum_{i=1}^{N}(X'_i - X)^2;$$

wherein N is a number of the plurality of noisy images, $X'_i$ is one of the plurality of noisy images, and X is the image reconstructed in step b).

8. The method as recited in claim 1 further comprising calculating weighting factors from the statistical noise map, the weighting factors indicating weighting values that when applied to the data acquired in step a) reduce contributions of noise in the acquired data.

9. The method as recited in claim 8 in which the weighting factors are calculated by producing noise variance projections by forward projecting the statistical noise map produced in step e) and fitting the noise variance projections to a weighting function.

10. The method as recited in claim 9 in which the weighting function is a monotonically decreasing function that assigns a lower weight to high noise data and a higher weight to lower noise data.

11. The method as recited in claim 1 in which the x-ray imaging system is at least one of an x-ray computed tomography system, an x-ray tomosynthesis system, a C-arm x-ray imaging system, and an on-board imaging system that forms a part of an image guided radiation therapy system.

12. The method as recited in claim 1 further comprising reconstructing an image from the data acquired in step a) using an iterative image reconstruction that accounts for a physical model of noise in the acquired data by using the statistical noise map produced in step e).

13. A method for iteratively reconstructing an image of a subject from data acquired with an x-ray imaging system, the steps of the method comprising:

a) acquiring data form the subject with the x-ray imaging system, the acquired data indicating a count of photons detected by the x-ray imaging system;

b) reconstructing an image from the data acquired in step a);

c) forming noisy data by adding statistical noise to the data acquired in step a);

d) reconstructing a noisy image from the noisy data formed in step c);

e) producing a statistical noise map using the image reconstructed in step b) and the noisy image reconstructed in step d); and f) reconstructing an image of the subject from the data acquired in step a) using an iterative image reconstruction that accounts for a physical model of noise in the acquired data by using the statistical noise map produced in step e).

14. The method as recited in claim 13 in which the noisy data formed in step c) comprises a plurality of noisy data sets, each noisy data set being formed by adding different statistical noise to the data acquired in step a).

15. The method as recited in claim 14 in which step d) includes reconstructing a plurality of noisy images from the noisy data, each noisy image being reconstructed from a corresponding noisy data set.

16. The method as recited in claim 15 in which step e) includes producing a plurality of statistical noise maps that each depict substantially only noise, each of the plurality of statistical noise maps being produced by subtracting one of the plurality of noisy images reconstructed in step d) from the image reconstructed in step b).

17. The method as recited in claim 16 in which step e) includes producing the statistical noise map by calculating an average of a sum of squares according to:

$$\frac{1}{N-1}\sum_{i=1}^{N}(X'_i - X)^2;$$

wherein N is a number of the plurality of noisy images, $X'_i$ is one of the plurality of noisy images, and X is the image reconstructed in step b).

18. The method as recited in claim 13 further comprising calculating weighting factors from the statistical noise map, the weighting factors that when applied to the data acquired in step a) reduce contributions of noise in the acquired data.

19. The method as recited in claim 18 in which the weighting factors are calculated by producing noise variance projections by forward projecting the statistical noise map produced in step e) and fitting the noise variance projections to a weighting function.

20. The method as recited in claim 19 in which the weighting function is a monotonically decreasing function that assigns a lower weight to high noise data and a higher weight to lower noise data.

21. The method as recited in claim 19 in which the noise variance projections are formed by forward projecting the statistical noise map onto a different acquisition geometry than was used to acquire the data in step a).

22. The method as recited in claim 18 in which step f) includes forming noise-suppressed projections by applying the weighting factors to the data acquired in step a) and reconstructing the image of the subject using the noise-suppressed projections.

23. The method as recited in claim 13 in which the x-ray imaging system is at least one of an x-ray computed tomography system, an x-ray tomosynthesis system, a C-arm x-ray imaging system, and an on-board imaging system that forms a part of a radiation therapy system.

* * * * *